United States Patent
Harano et al.

(10) Patent No.: US 6,855,142 B2
(45) Date of Patent: Feb. 15, 2005

(54) ELECTROSURGICAL DEVICE FOR TREATING BODY TISSUE WITH HIGH-FREQUENCY POWER

(75) Inventors: Kenji Harano, Hachioji (JP); Masahide Ohyama, Hino (JP); Kazuya Hijii, Hachioji (JP); Shinji Hatta, Hachioji (JP)

(73) Assignee: Olympus Corporation, Tokyo (JP)

( * ) Notice: Subject to any disclaimer, the term of this patent is extended or adjusted under 35 U.S.C. 154(b) by 24 days.

(21) Appl. No.: 10/135,125

(22) Filed: Apr. 29, 2002

(65) Prior Publication Data

US 2002/0165530 A1 Nov. 7, 2002

(30) Foreign Application Priority Data

May 7, 2001 (JP) ........................................ 2001-136533

(51) Int. Cl.$^7$ .............................................. A61B 18/18
(52) U.S. Cl. .......................................... 606/40; 128/898
(58) Field of Search ..................................... 606/27–52

(56) References Cited

U.S. PATENT DOCUMENTS 5,947,964 A * 9/1999 Eggers et al. ................. 606/41
5,971,980 A * 10/1999 Sherman ....................... 606/34
6,063,075 A * 5/2000 Mihori ........................ 606/35

FOREIGN PATENT DOCUMENTS

JP 8-98845 4/1996
JP 10-225462 8/1998

* cited by examiner

Primary Examiner—Michael Peffley
Assistant Examiner—Peter J Vrettakos
(74) Attorney, Agent, or Firm—Scully, Scott, Murphy & Presser

(57) ABSTRACT

An electrosurgical device for treating a body tissue with a high-frequency power includes an electrode for exposing the body tissue to the high-frequency power for treatment, and a high-frequency cautery power supply having a control circuit that outputs a high-frequency power generator for outputting the high-frequency power to the electrode. The control circuit of the high-frequency cautery power supply includes a timer for measuring output time and suspension time of the high-frequency power applied to the body tissue, a counting unit for counting the number of output of the high-frequency power, an impedance detector for detecting an impedance of the body tissue in the coagulated state thereof when the body tissue is treated using the high-frequency power applied from the electrode, an impedance comparator for comparing the impedance of the coagulated tissue detected by the impedance detector with an impedance predetermined for the purpose of the treatment of a region to be treated, and a high-frequency power switch for switching the output of the high-frequency power generator.

16 Claims, 10 Drawing Sheets

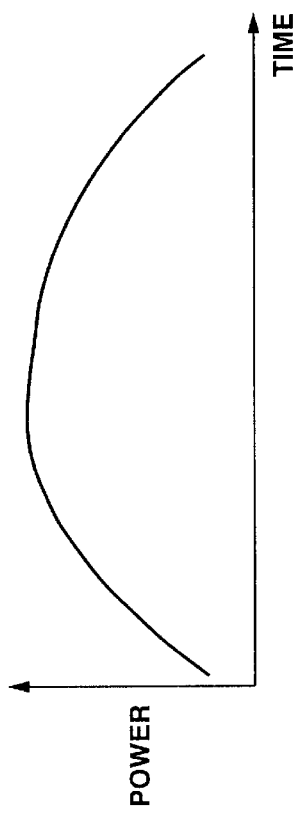
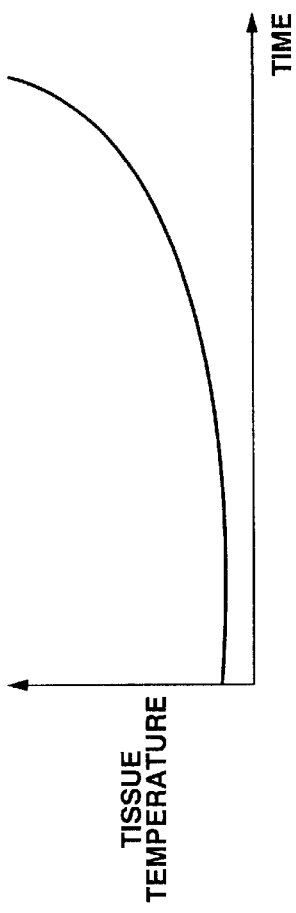
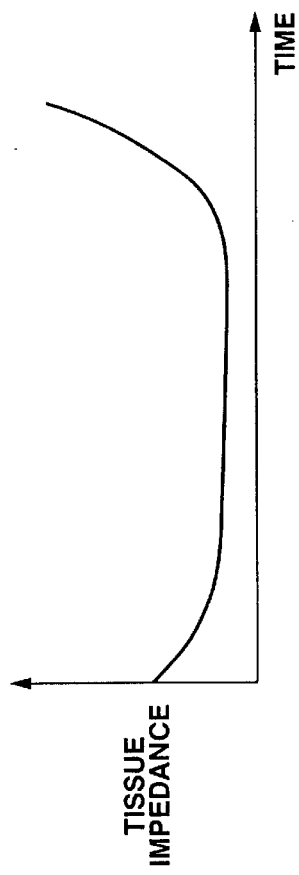
FIG.1A (PRIOR ART)
FIG.1B (PRIOR ART)
FIG.1C (PRIOR ART)

COAGULATION

INCISION

ELECTROSURGICAL DEVICE FOR TREATING BODY TISSUE WITH HIGH-FREQUENCY POWER

This application claims benefit of Japanese Application No. 2001-136533 filed on May 7, 2001, the contents of which are incorporated by this reference.

BACKGROUND OF THE INVENTION

1. Field of the Invention

The present invention relates to an electrosurgical device having a control unit for controlling a high-frequency power output having a unique operational pattern.

2. Description of the Related Art

Electrosurgical devices such as a cautery knife is typically used to incise, coagulate, and blood stanch a body tissue in a surgical operation or a medical surgical operation. Such electrosurgical device includes a high-frequency cautery power supply and an instrument connected to the high-frequency cautery power supply. The electrosurgical device treats a body tissue of a patient with the high-frequency power supply applying the high-frequency power to the body tissue through the instrument which is in contact with the body tissue.

When the high-frequency power is applied onto the body tissue by the electrosurgical device, the body tissue is heated, and proteins thereof is denatured. The tissue is then dried with the moisture therewithin evaporated. In this process, the body tissue is coagulated. By continuously applying the high-frequency power to the body tissue even after the moisture contained therewithin is evaporated, the tissue is carbonized. The body tissue then begins to stick to the instrument. To prevent the body tissue from sticking to the instrument, the supply of the high-frequency power must be stopped when the body tissue starts being dried.

An electrosurgical device disclosed in Japanese Unexamined Patent Application Publication No. 8-98845 determines the end of coagulation referring to the tissue impedance of the body tissue and then stops the supply of the high-frequency power in order to prevent the body tissue from being carbonated and from sticking to an instrument.

To achieve the same object of Japanese Unexamined Patent Application Publication No. 8-98845, an electrosurgical device disclosed in Japanese Unexamined Patent Application Publication No. 10-225462 lowers a high-frequency output power.

In these conventional electrosurgical devices, the high-frequency power is applied to the body tissue as shown in FIG. 1A. The body tissue exposed to the high-frequency power is then heated as shown in FIG. 1B. The tissue temperature rapidly rises as the protein of the body tissue is denatured and the drying of the body tissue is in progress. Referring to FIG. 1C, the tissue impedance initially drops and then rapidly rises as the body tissue is dried.

The conventional electrosurgical device stops the supply of the high-frequency power at the moment the dried state is detected from the tissue impedance or the tissue temperature.

The conventional electrosurgical device outputs a rated power if the tissue impedance is in the vicinity of the rated value thereof. When the tissue impedance is deviated from the rated value thereof, the high-frequency power sharply drops in level. The electrosurgical device thus takes time to heat the body tissue to a desired temperature because of the drop of the high-frequency power.

When the body tissue to be coagulated is very large in size, the electrosurgical device must output the high-frequency power for a long period of time. This leads to an excessive temperature rise in the body tissue, thereby causing the body tissue to stick to the instrument.

SUMMARY OF THE INVENTION

Accordingly, it is an object of the present invention to provide an electrosurgical device that works with a short overall output time of a high-frequency power and reliably coagulates a body tissue.

It is a second object of the present invention to provide an electrosurgical device that reliably coagulates the body tissue while reducing the possibility of the body tissue sticking to an instrument.

An electrosurgical device of the present invention for treating a body tissue with a high-frequency power includes an electrode for outputting a high-frequency power to the body tissue for treatment, and a high-frequency cautery power supply having a control circuit for controlling a high-frequency power generator that outputs the high-frequency power to the electrode. The control circuit of the high-frequency cautery power supply includes a time measurement unit for measuring output time and suspension time of the high-frequency power applied to the body tissue, a counting unit for counting the number of output of the high-frequency power, an impedance detector for detecting an impedance of the body tissue in the coagulated state thereof when the body tissue is treated using the high-frequency power applied from the electrode, an impedance comparator for comparing the impedance of the coagulated tissue detected by the impedance detector with an impedance predetermined for the purpose of the treatment of a region to be treated, and a high-frequency power switch for switching the output of the high-frequency power generator based on the result of comparison provided by the impedance comparator.

The electrosurgical device reliably coagulates the body tissue while reducing the possibility of the body tissue sticking to an instrument.

The above and other objects, features and advantages of the invention will become more clearly understood from the following description referring to the accompanying drawings.

BRIEF DESCRIPTION OF THE DRAWINGS

FIG. 1A is a graph showing the relationship between a high-frequency power and time in a conventional electrosurgical device;

FIG. 1B is a graph showing the relationship between the tissue temperature of a body tissue and time in the conventional electrosurgical device;

FIG. 1C is a graph showing the relationship between the tissue impedance and time in the conventional electrosurgical device;

FIG. 2 generally illustrates an electrosurgical device of the first embodiment;

FIG. 3 is a block diagram illustrating a high-frequency cautery power supply of the electrosurgical device;

FIG. 4 is a flow diagram illustrating a control flow of a control circuit;

FIG. 5 illustrates the operation of the electrosurgical device in accordance with the flow diagram illustrated in FIG. 4, showing the output voltage and the output power of high-frequency power, and the temperature and impedance of a body tissue with respect to time;

FIG. 6 is a flow diagram showing another control flow of the control circuit;

FIG. 7 illustrates the operation of the electrosurgical device in accordance with the flow diagram illustrated in FIG. 6;

FIG. 8 is a flow diagram illustrating the control flow of the control circuit;

FIG. 9 illustrates the operation of the electrosurgical device in accordance with the flow diagram illustrated in FIG. 8, showing the output voltage and the output power of high-frequency power, and the temperature and impedance of a body tissue with respect to time;

DETAILED DESCRIPTION OF THE PREFERRED EMBODIMENTS

The embodiments of the present invention are discussed below with reference to the drawings.

Referring to FIGS. 2 through 7, a first embodiment of the present invention is discussed.

Figure 2:
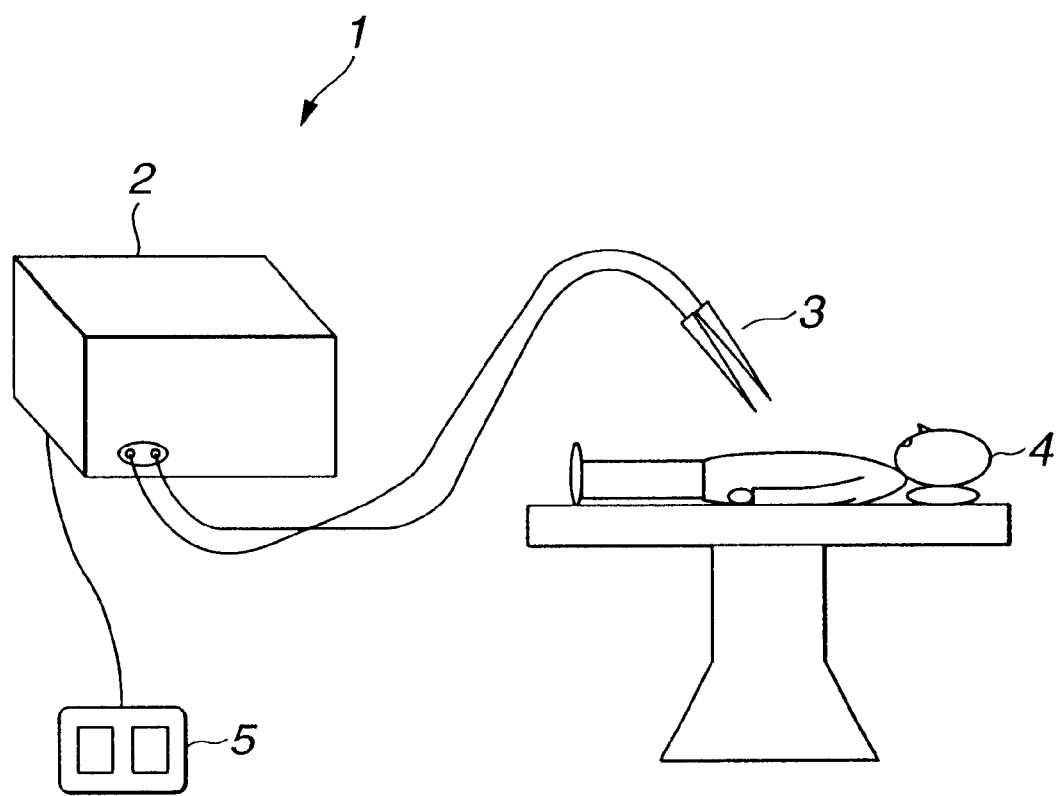
FIGS. 2 through 7 illustrate a first embodiment of the present invention.

Referring to FIG. 2, an electrosurgical device 1 includes a high-frequency cautery power supply 2 and a pair of electrodes 3 as an instrument which applies a high-frequency power to the body tissue of a patient from the high-frequency cautery power supply 2.

The high-frequency cautery power supply 2 is connected to a foot switch 2a for turning on and off the application of the high-frequency power. The pair of electrodes 3 grip the body tissue of the patient to apply the high-frequency power to the body tissue therebetween. The electrodes 3 may has a single-electrode structure or a multiple-electrode structure.

Figure 3:
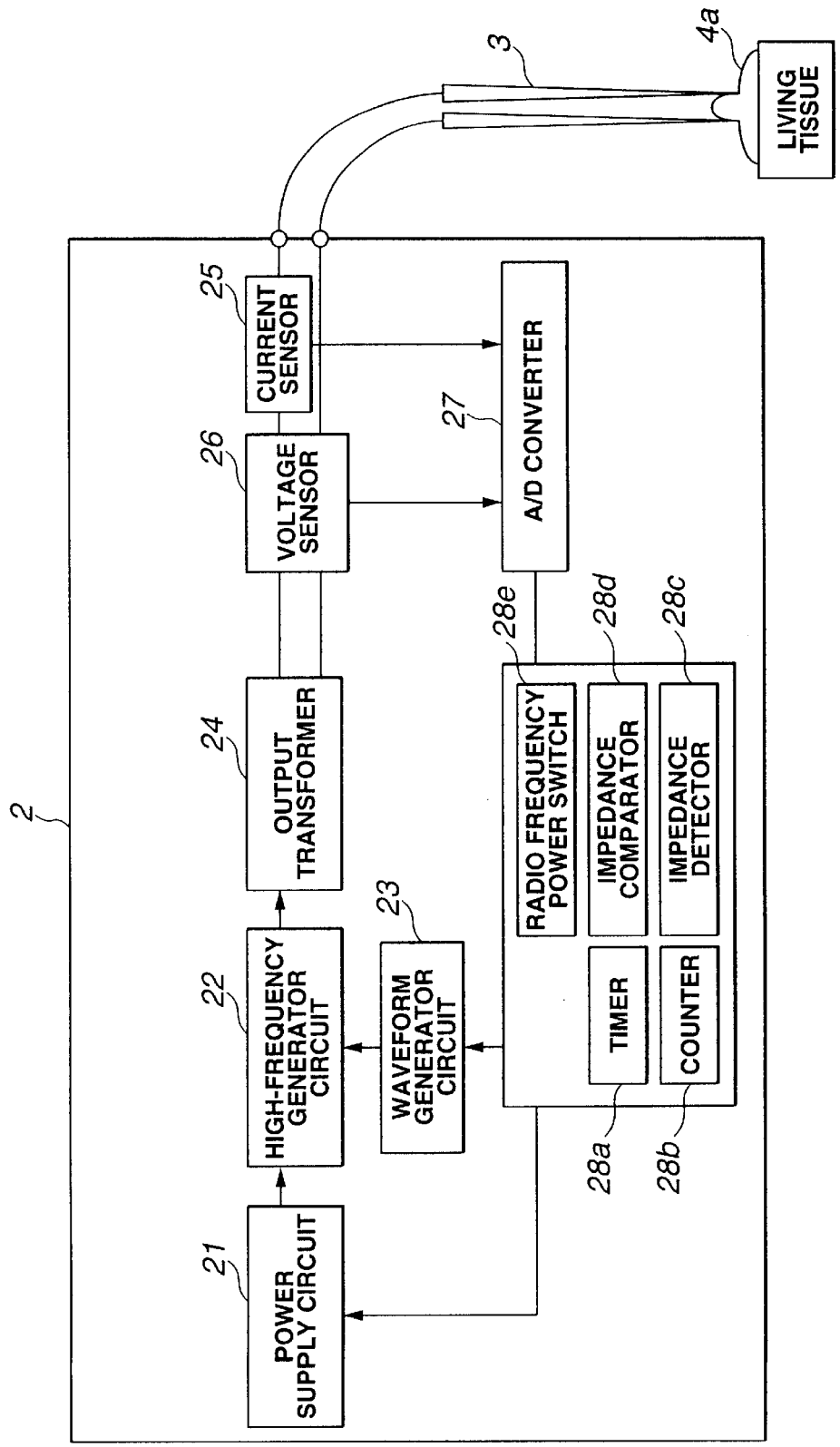

Referring to FIG. 3, the high-frequency cautery power supply 2 includes a power supply 21, a high-frequency generator 22 for generating a high-frequency power, a waveform generator 23, an output transformer 24, a current sensor 25, a voltage sensor 26, an A/D converter 27, and a control circuit 28.

The power supply 21 feeds a DC current. The high-frequency generator 22 converts the DC current from the power supply 21 into a high-frequency current. The waveform generator 23 controls the high-frequency generator 22 to shape the waveform of the high-frequency current. The output transformer 24 outputs the high-frequency current from the high-frequency generator 22 to the electrodes 3. The current sensor 25 detects the output current from the output transformer 24. The voltage sensor 26 detects the output voltage output by the output transformer 24. The A/D converter 27 analog-to-digital converts the current value and the voltage value respectively detected by the current sensor 25 and the voltage sensor 26. The control circuit 28 controls the power supply 21 and the waveform generator 23 based on the current and voltage values digitized by the A/D converter 27.

The control circuit 28 includes a timer 28a as a time measurement unit, a counter 28b as a counting unit, an impedance detector 28c, an impedance comparator 28d, and a high-frequency power switch 28e.

The timer 28a measures output time and suspension time of the output of the high-frequency current applied to the body tissue. The counter 28b counts the output of the high-frequency current. The impedance detector 28c is coagulated state detector means for detecting a coagulated state of the body tissue based on the current and voltage data, body information such as the impedance and temperature of the body tissue, and the output of the high-frequency current to be discussed later. The impedance comparator 28d is coagulated state determination means for comparing the coagulated state value detected by the impedance detector 28c with a predetermined coagulated state value. The high-frequency power switch 28e is high-frequency power output control means for controlling the high-frequency power output by the high-frequency generator 22 to a smaller value or to a larger value.

The information about the coagulated state of the body tissue determined by the control circuit 28 is presented on a monitor (not shown) as display means, or a liquid-crystal panel (not shown) arranged oh the high-frequency cautery power supply 2.

The high-frequency cautery power supply 2 in the first embodiment is designed to feed a constant high-frequency power (constant power output Wc) not influenced by the tissue impedance.

The operation of the electrosurgical device of the first embodiment is discussed with reference to a flow diagram illustrated in FIG. 4.

Figure 4:
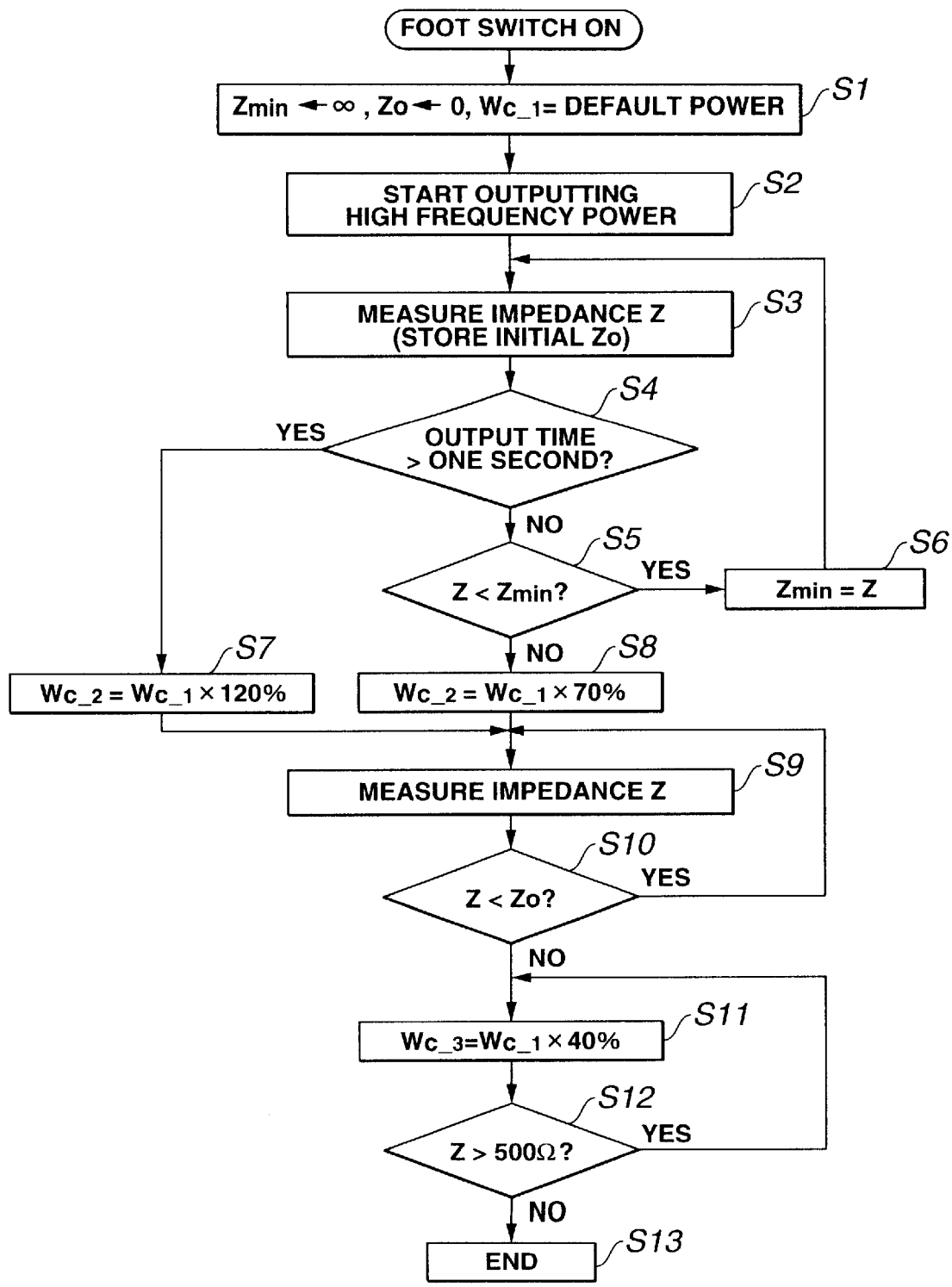

When the foot switch 2a is pressed for an on operation with the electrodes 3 gripping the body tissue of a patient, the control circuit 28 controls the electrosurgical device in accordance with the flow diagram illustrated in FIG. 4.

In step S1, the minimum value Zmin of the tissue impedance is set to be infinity, the initial tissue impedance Z0 is set to be zero, and power Wc_1 is set to be a default power value during the high-frequency power output.

The set power Wc_1 is set to be any default power taking into account the tissue temperature and the volume of the body tissue.

In step S2, the output of the high-frequency power starts. The timer 28a is turned on at the same moment the output of the high-frequency power starts, thereby starting measuring the output time. In step S3, the signals are captured from the current sensor 25 and the voltage sensor 26 through the A/D converter 27. The tissue impedance Z of the body tissue is calculated and stored into a memory (not shown). The initial tissue impedance Z0 is also stored into the memory.

In step S4, it is determined whether the output time exceeds one second. When it is determined that the output time does not exceed one second, the algorithm proceeds to step S5. The tissue impedances Z successively obtained are compared with the minimum value Zmin. When the tissue impedance Z is smaller than the minimum value Zmin, the algorithm proceeds to step S6 to successively correct the minimum value Zmin. The algorithm loops to step S3, thereby repeating the same steps.

When the output time exceeds one second in step S4, the control circuit 28 determines that the volume of the body tissue gripped by the electrodes 3 is large, and the algorithm proceeds to step S7. In step S7, the output power of the high-frequency power is set to be Wc_2=Wc_1×120%, and the electrosurgical device reverts to the outputting of the high-frequency power.

When the tissue impedance Z is greater than the minimum value Zmin in step S5, the algorithm proceeds to step S8. The output power of the high-frequency output is set to Wc_2=Wc_1×70%, and the electrosurgical device reverts to the outputting of the high-frequency power.

The control circuit 28 measures the tissue impedance z in step S9 again, and proceeds to step S10. The tissue impedance Z measured in step S10 is compared with the initial tissue impedance Z0. When the tissue impedance Z is smaller than the initial tissue impedance Z0, steps S9 and S10 are repeated until the tissue impedance Z becomes larger than the initial tissue impedance Z0.

When the tissue impedance Z becomes larger than the initial tissue impedance Z0 in step S10, the algorithm proceeds to step S11. The output power of the high-frequency power is set to be Wc_3=Wc_1×40%, and the electrosurgical device reverts to the output of the high-frequency power.

It is determined in step S12 whether the tissue impedance Z is less than a predetermined value, for example, 500 Ω. Steps S11 and S12 are repeated until the tissue impedance becomes equal to or larger than 500 Ω. When the tissue impedance Z exceeds 500 Ω in step S12, the control circuit 28 stops the output of the high-frequency power and ends the process.

An operator may set the control parameters in the control process, such as the output time of one second in step S4 and the tissue impedance Z of 500 Ω in step S12, to any values.

The user may set a percentage set for Wc_2 in steps S7 and S8 and a percentage set for Wc_3 in step S11 to any value.

The control circuit 28 sets the output of the high-frequency power to be constant and free from the tissue impedance of the body tissue, and performs a fine control process taking into account the initial output power in the initial phase of power control and the high-frequency power in the last phase of power control and the tissue volume of the body tissue held between the electrodes 3.

Figure 5:
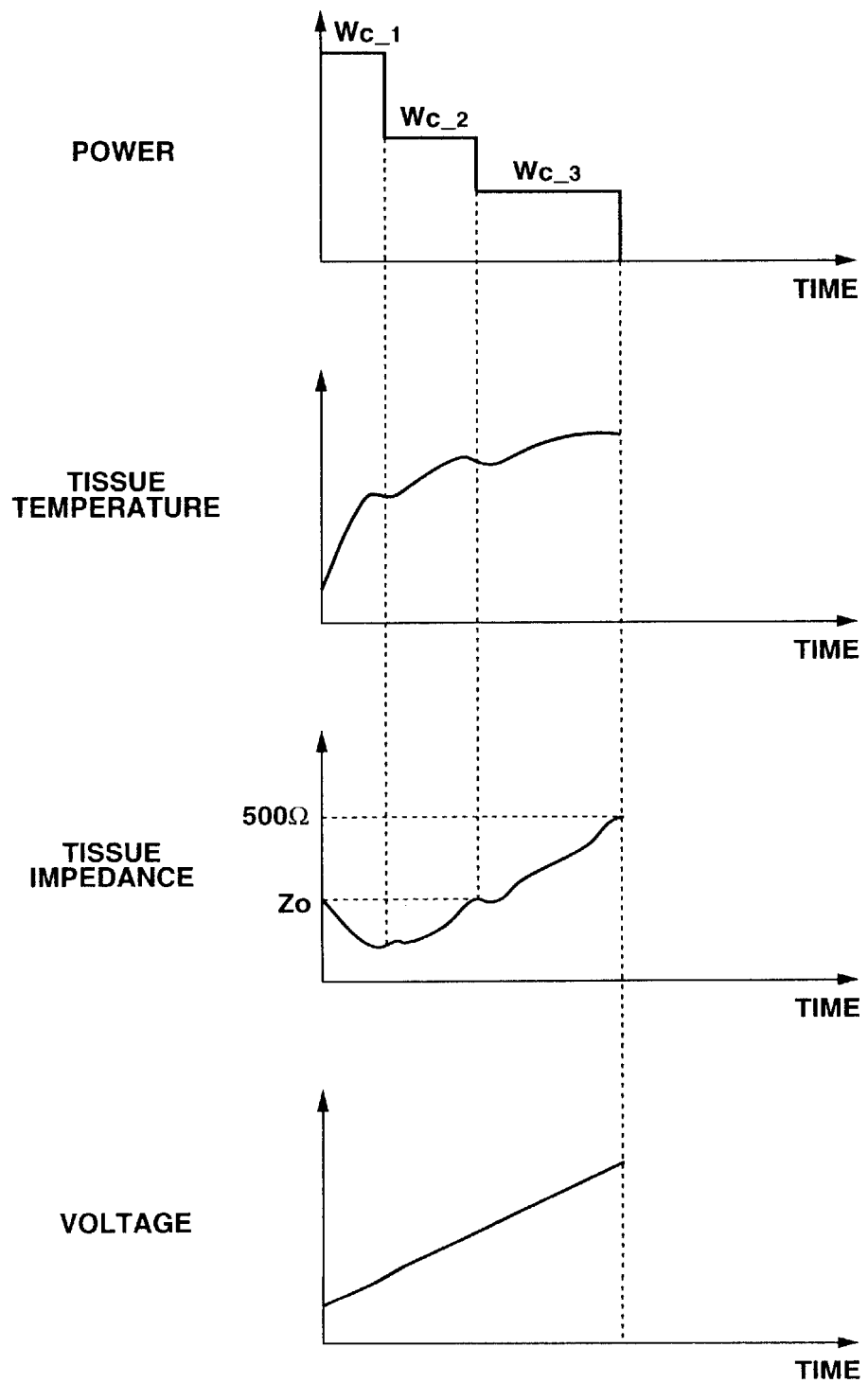

In the above control process, the output voltage and the output power of the high-frequency power, the tissue temperature of the body tissue and the tissue impedance are varied with respect to time as shown in FIG. 5.

As discussed above, the tissue temperature rises when the high-frequency power at the default power Wc_1 is applied. The tissue impedance Z initially drops down to the minimum value Zmin and then rises. If the tissue impedance Z becomes larger than the minimum value Zmin within one second of the output time as in step S4, the high-frequency power is output at Wc_2=Wc_1×70%.

The tissue temperature and the tissue impedance Z then slightly drop, and then rise again. The high-frequency power is continuously output at Wc_2 until the tissue impedance Z reaches the initial tissue impedance Z0.

When the tissue impedance Z reaches the initial tissue impedance Z0, the outputpower of the high-frequency power is set to from Wc_2 to Wc_3=Wc_1×40%, and is output. In the same way as with the output power Wc_2, the tissue temperature and the tissue impedance Z slightly drop, and then rise again. The high-frequency output power of Wc_3 is continuously output until the tissue impedance Z becomes equal to or larger than a predetermined value, for example, 500 Ω. When the tissue impedance Z becomes equal to or larger than 500 Ω,the process ends.

The output voltage of the high-frequency power rises at a constant rate.

Since the output power of the high-frequency power is varied from Wc_1, to Wc_2 to Wc_3, the tissue temperature, the tissue impedance, and the output voltage are prevented from rapidly rising in the last phase of power application. This arrangement prevents the body tissue from being carbonized, and from sticking to the electrodes.

Because of its constant level, the high-frequency output power is fed at an intended level without being influenced by the tissue impedance. The electrosurgical device thus completes the treatment of the body tissue within a short overall output time.

Figure 6:
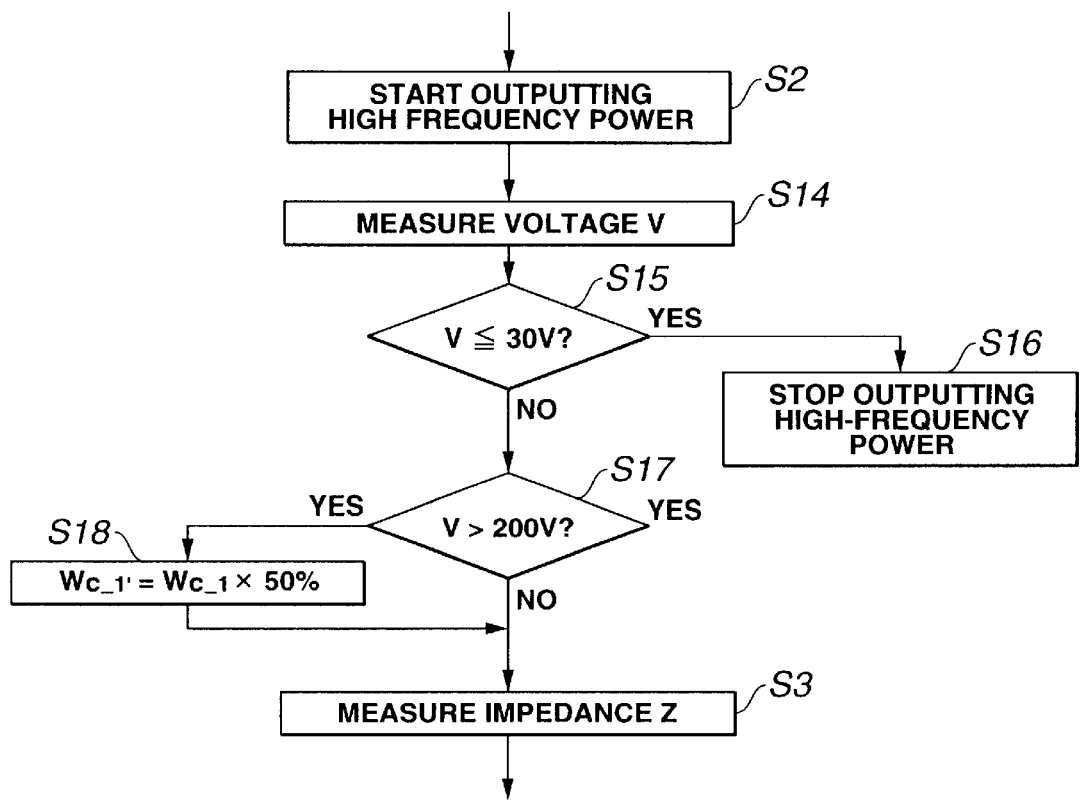

Referring to FIG. 6, another control process for the output voltage of the high-frequency power may be added between steps S2 and S3 in the flow diagram illustrated in FIG. 4.

Referring to FIG. 6, the control circuit 28 measures the output voltage V of the high-frequency power with the voltage sensor 26 in step S14 immediately subsequent to step S2 in which the output of the high-frequency power at the default power Wc_1 starts. The process then proceeds to step S15.

In step S15, the control circuit 28 determines whether the output voltage is equal to or lower than a predetermined voltage, for example, 30 V. When the output voltage is equal to or lower than 30 V, the control circuit 28 determines that the electrodes 3 are in contact with each other or that there is a shortcircuit within the electrodes 3 or in the high-frequency cautery power supply 2. The control circuit 28 then entirely stops the output of the high-frequency power in step S16.

When the output voltage V of the high-frequency power is higher than 30 V in step S15, the control circuit 28 determines that there is no shortcircuit, and then proceeds to step S17. In step S17, the control circuit 28 determines whether the output voltage is higher than a predetermined value, for example, 200 V. When the control circuit 28 determines that the output voltage V is higher than 200 V, the default power is high. The control circuit 28 thus determines that the body tissue gripped by the electrodes has a small volume or is carbonized. In step S18, the high-frequency output power is set to be 50% of the default power Wc_1, and is then output.

When the output voltage of the high-frequency power is equal to or lower than 200 V, the control circuit 28 determines that the operation is normal, and then proceeds to step S3. The steps to be performed thereafter remain unchanged from those illustrated in the flow diagram in FIG. 4.

The operator may set control parameters in the control process, such as the output voltages V of the high-frequency power, for example, 30 V and 200 V in step S15 and step S17, to any values. The operator may also set a percentage for the default power Wc_1 in step S18 to any value.

Figure 7:
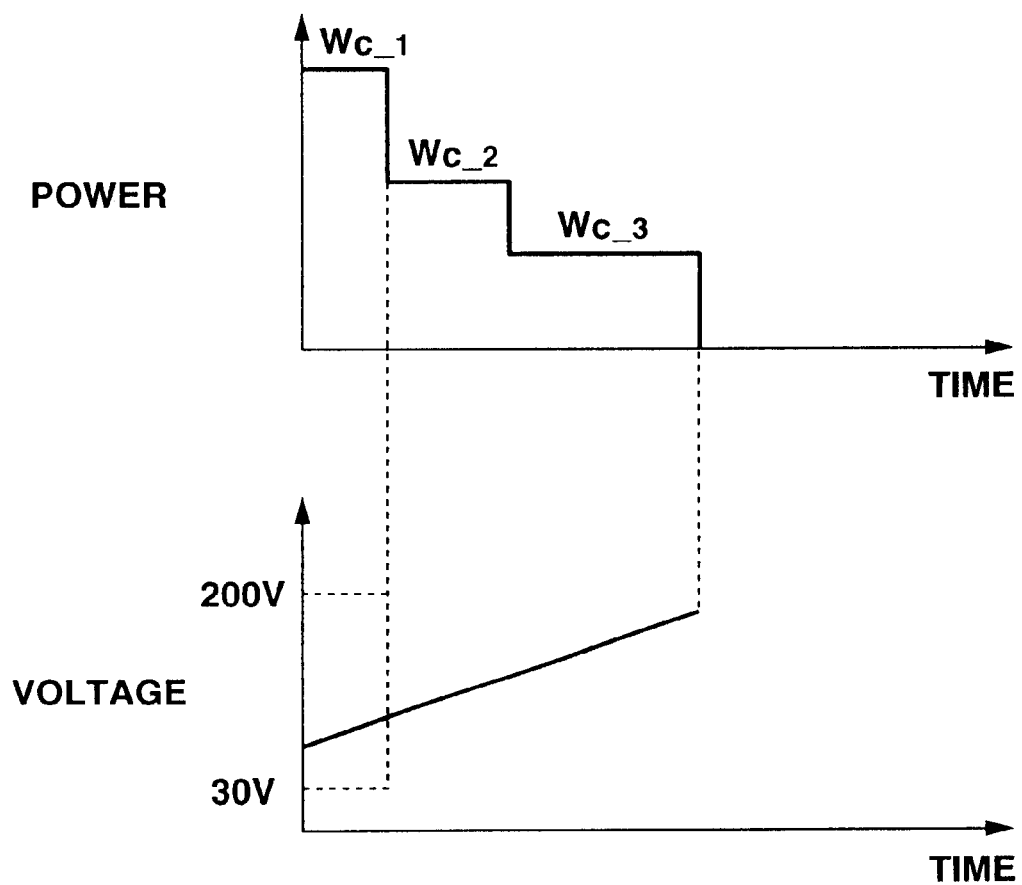

FIG. 7 illustrates the output voltage and power of the high-frequency output signal with respect to time in the above control process.

As discussed above, when the measured output voltage is higher than 30 V but equal to or lower than 200 V immediately subsequent to the supply of the high-frequency power at the default power Wc_1, the high-frequency power is continuously output at the default power Wc_1.

When the output voltage is lower than the predetermined value, for example, 30 V, the output of the high-frequency power is stopped. The high-frequency output power is reduced to 50% of the default power Wc_1 (Wc_1'=Wc_

1×50%) when the output voltage is higher than the predetermined value, for example, 200 V, although the reduced voltage is not shown.

In the above modification, a shortcircuit is detected from the output voltage of the high-frequency power. In this way, an automatic correction process may be activated if there occurs a problem that predictably outputs a high power in the initial phase.

The electrosurgical device of the first embodiment provides a constant power, and heightens the default power in the initial phase during which the moisture of the body tissue is abundant, and lowers the default power in the phase during which a coagulation is in progress.

The electrosurgical device of the first embodiment allows the body tissue to coagulate for a short period of time. Since the electrosurgical device cauterizes the tissue surface of the body tissue with a high power for a short period of time in the initial phase of the power application, the amount of tissue sticking to the electrodes is reduced. For a long period of time in the last phase of power application, a low high-frequency power is applied to heat the body tissue, thereby promoting coagulation. Since the volume of the body tissue gripped by the electrodes is detected and is used as a reference to raise and lower the high-frequency power in level, automatic power control is performed in an optimum way.

The electrosurgical device of the first embodiment varies the high-frequency power in level in accordance with the coagulated state and the volume of the body tissue in a short period of time, thereby reducing the amount of tissue sticking to the electrode and preventing the body tissue from being carbonized. High coagulation performance is thus achieved.

Figure 8:
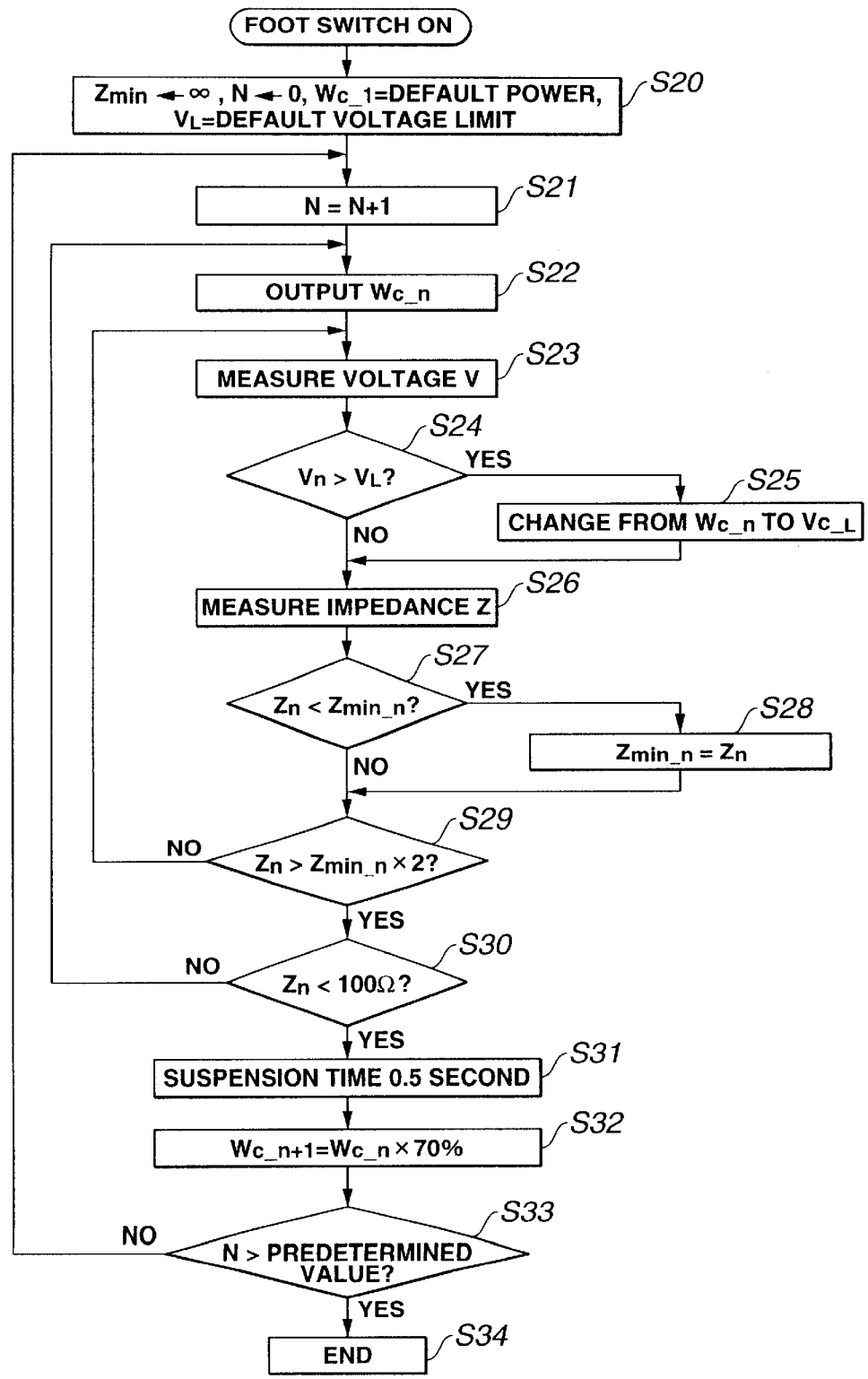
FIGS. 8 and 9 illustrate a second embodiment of the present invention.

A second embodiment of the present invention is discussed below with reference to FIGS. 8 and 9.

In the first embodiment, power control is performed so that the constant high-frequency power output is heightened in the initial phase of power application, and is lowered in the phase in which coagulation is in progress. In the second embodiment, power control is performed so that constant high-frequency power is output in an on and off fashion. The rest of the second embodiment remains unchanged from the first embodiment, and the discussion thereof is omitted here. The operation of the control circuit 28 is discussed with reference to a flow diagram shown in FIG. 8.

As already discussed in connection with the first embodiment, the electrodes 3 hold the body tissue of a patient, and the foot switch 2a is turned on.

With the foot switch 2a turned on, at the initial output of the high-frequency power, the control circuit 28 sets the minimum value Zmin of the tissue impedance to infinity, the output N to zero, the default power Wc_1 and the default voltage limit VL to respective predetermined values in step S20.

The default power Wc_1 and the output count N may be set to any values accounting for the tissue temperature and the volume of the body tissue.

In step S21, the counter 28b counts up the output N, and the electrosurgical device starts outputting the high-frequency power at the default power Wc_1 in step S22. At the same moment the outputting of the high-frequency power starts, the timer 28a is turned on, starting measuring the output time.

The control circuit 28 captures a signal from the voltage sensor 26 through the A/D converter 27 in step S23, and compares the output voltage Vn of the high-frequency power with the default voltage limit VL in step S24.

When the output voltage Vn of the high-frequency power is higher than the default voltage limit VL, the control circuit 28 proceeds to step S25 to prevent shortcircuit. The control circuit 28 changes the power control mode of the high-frequency power from the constant power Wc_1 control to the constant voltage Vc_L control, and then proceeds to step S26.

When the output voltage Vn of the high-frequency power is lower than the default voltage limit VL in step S24, the algorithm directly proceeds to step S26.

In step S26, the control circuit 28 obtains the signals from the current sensor 25 and the voltage sensor 26, and calculates and stores the tissue impedance Zn of the body tissue into a memory (not shown).

In step S27, the control circuit 28 compares the tissue impedance Zn with the minimum value Zmin_n. When the tissue impedance Zn is lower than the minimum value Zmin_n, the control circuit 28 substitutes Zn for the minimum value Zmin_n, thereby successively updating the minimum value Zmin_n in step S28. When the tissue impedance Zn is higher than the minimum value Zmin_n in step S27, the algorithm directly proceeds to step S29.

In step S29, the control circuit 28 determines whether the tissue impedance Zn rises above twice the minimum value Zmin_n, namely, Zmin_n×2. When it is determined that the tissue impedance Zn is less than Zmin_n×2, the algorithm loops to S23, and the above steps are repeated. When it is determined that the tissue impedance Zn rises above Zmin_n×2, the algorithm proceeds to step S30.

In step S30, the control circuit 28 determines whether the tissue impedance Zn rises above a predetermined value, for example, 100 Ω. When the tissue impedance Z is lower than 100 Ω, the control circuit 28 determines that the body tissue is not fully coagulated. The algorithm loops to step S22 to repeat the above steps. Specifically, the outputting of the high-frequency power at Wc_n is performed repeatedly.

When it is determined in step S30 that the tissue impedance Zn rises above 100 Ω, the algorithm proceeds to step S31. The outputting of the high-frequency power is suspended for 0.5 second, and after the suspension time of 0.5 second, the algorithm proceeds to step S32.

In step S32, the control circuit 28 outputs the high-frequency power at Wc_n+1=Wc_n×70%.

In step S33, the control circuit 28 determines whether the output count N reaches a predetermined count. When it is determined that the output count N has yet to reach the predetermined count, the algorithm loops to step S21 to repeat the above steps. The above steps are repeated until the output count N reaches the predetermined count. When the output count N reaches the predetermined count, the control circuit 28 stops the outputting of the high-frequency power and ends the process.

The operator may set control parameters in the control process, such as the default voltage limit VL in step S24, the suspension time of 0.5 second in step S31, and the predetermined value 100 Ω as the tissue impedance Zn in step S30 to any values. The operator may also set a percentage for the Wc_n+1 in step S32 to any value.

Figure 9:
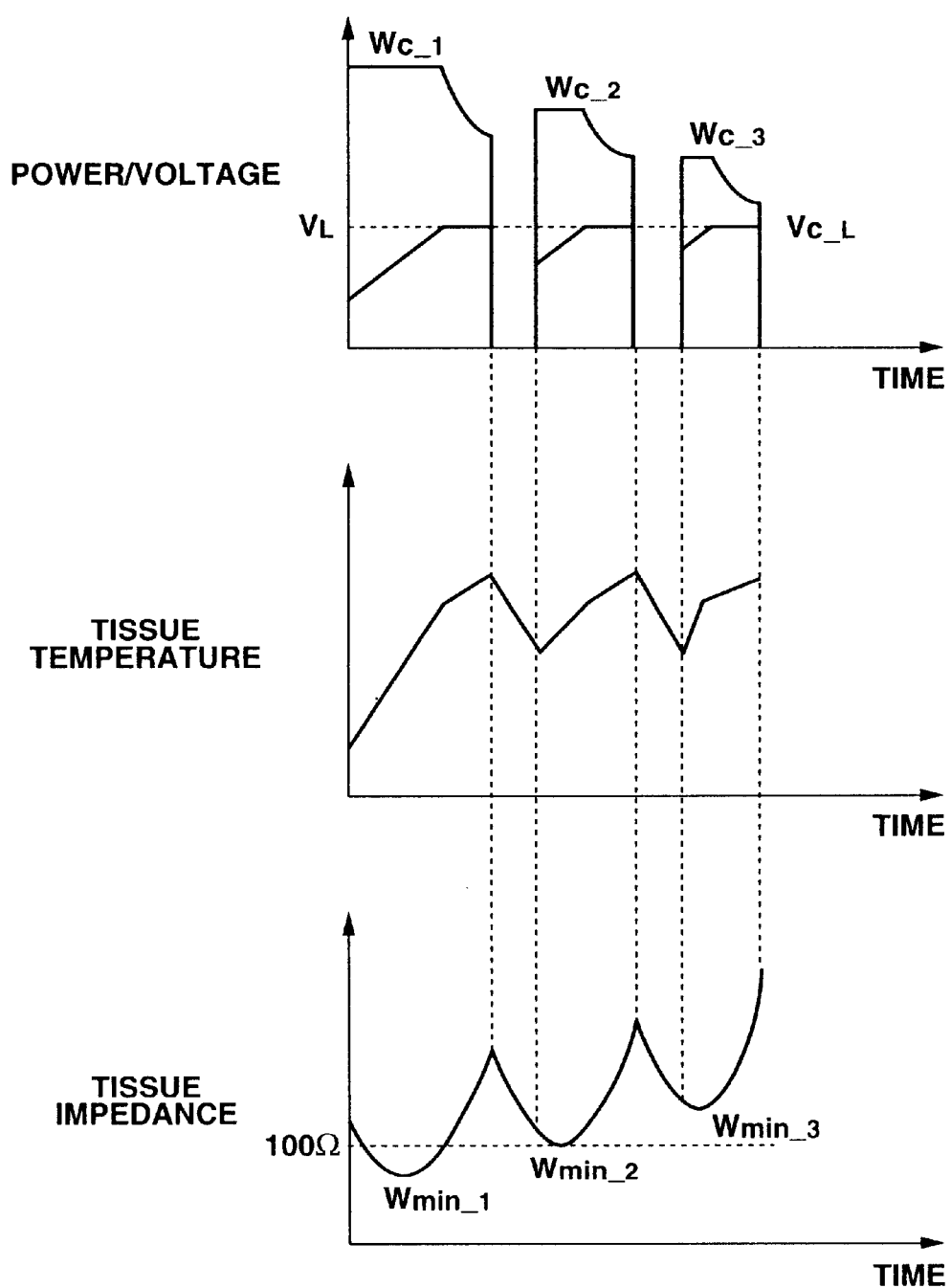

In the above control process, the output voltage and the output power of the high-frequency power, the tissue temperature of the body tissue and the tissue impedance are varied with respect to time as shown in FIG. 9.

As discussed above, the tissue temperature rises when the high-frequency power at the default power Wc_1 is applied.

The tissue impedance Zn initially drops down to the minimum value Zmin_n and then rises. When the output voltage Vn of the high-frequency power rises above the default voltage limit VL, the control circuit 28 shifts power control mode from constant power Wc_1 control to constant voltage Vc_L control.

One of the constant power Wc_1 control or the constant voltage Vc_L control is repeated until the tissue impedance Zn reaches 100 Ω after rising above twice the minimum value Zmin_1.

When the tissue impedance Zn rises above twice the minimum value Zmin_1, and then reaches 100 Ω, the outputting of the high-frequency power is suspended for 0.5 second. The tissue temperature drops, and the tissue impedance drops down to Zmin_2.

After the suspension time of 0.5 second, the high-frequency power is output again. The output of the high-frequency power Wc_2 is set to be Wc_2=Wc_1×70%. The tissue temperature and the tissue impedance Z rise again. This operation is repeated until the output count N reaches a predetermined output count.

The electrosurgical device switches on and off the high-frequency power, thereby performing a combination of the constant power Wc_1 control and the constant voltage Vc_L control. The electrosurgical device of the second embodiment feeds the maximum high-frequency power in response to the coagulated state of the body tissue without any shortcircuit involved. The body tissue is thus reliably coagulated within a short period of time.

With the suspension time permitted between the output, the upper temperature limit of the body tissue is controlled. The electrosurgical device of the second embodiment thus prevents the body tissue from sticking to the electrodes and from being carbonized.

Since the power control is performed based on the two quantities, namely, the rate of change and the predetermined value of the tissue impedance Z, the volume of the body tissue is accounted for.

The electrodes 3 connected to the high-frequency cautery power supply 2 are discussed below with reference to FIG. 10A and FIG. 11.

Figure 10A:
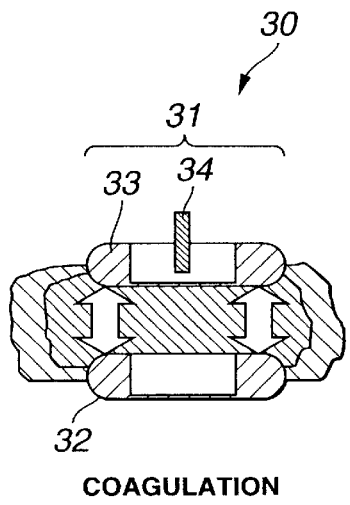
FIG. 10A is an enlarged end view of coagulating and incising electrodes which perform a coagulation process on a body tissue.
Figure 10B:
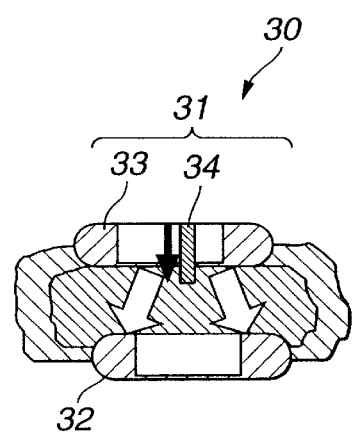
FIG. 10B is an enlarged end view of the coagulating and incising electrodes which perform a incision process on a body tissue.

Referring to FIGS. 10A and 10B, the pair of electrodes 3 are coagulating and incising electrodes 30 for coagulating and incising the body tissue.

The coagulating and incising electrodes 30 include feeder electrodes 31 for feeding the high-frequency power to the body tissue and a return electrode 32 for retrieving the high-frequency power supplied to the body tissue. The feeder electrodes 31 include a coagulating electrode 33 and an incising electrode 34.

When the body tissue is coagulated with the coagulating and incising electrodes 30, the coagulating electrode 33 is used. When the body tissue is incised, the incising electrode 34 is used. The incising electrode 34 is retracted within the coagulating electrode 33, and is projected by an unshown projecting mechanism.

The incising electrode 34 may be projected by the projecting mechanism controlled by the control circuit 28 discussed in connection with the first embodiment, or may be projected in response to a pressing operation of a pushbutton.

Figure 11:
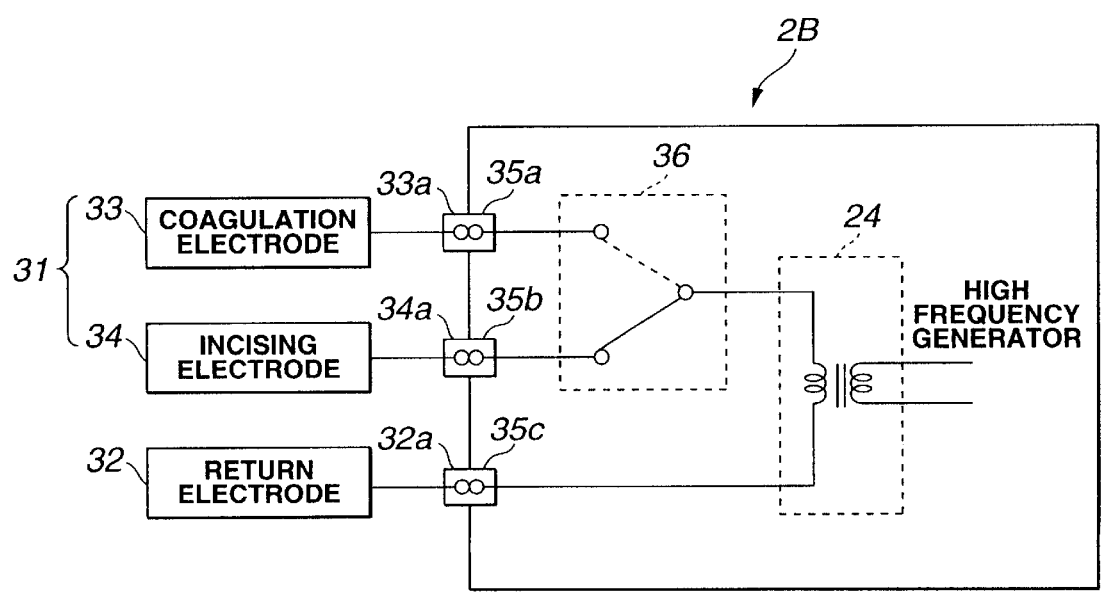
FIG. 11 is a circuit block diagram illustrating a major portion of a high-frequency cautery power supply.

Referring to FIG. 11, the high-frequency cautery power supply 2B to which the coagulating and incising electrodes 30 are connected, has connector sockets 35a, 35b, and 35c to which a return connector 32a of the return electrode 32, a coagulation connector 33a for the coagulating electrode 33, and an incising connector 34a for the incising electrode 34 are respectively mated.

In response to a switch 36, the high-frequency cautery power supply 2B performs one of the coagulation operation and the incising operation. Specifically, the switch 36 switches between the connector socket 35a for the coagulating electrode 33 and the connector socket 35b for the incising electrode 34 so that the power from the output transformer 24 is selectively supplied to the coagulating electrode 33 and the incising electrode 34.

The switch 36 may be controlled by the control circuit 28 discussed in connection with the first embodiment, or may be turned on in response to a pressing operation of a pushbutton.

The coagulating and incising electrodes 30 and the high-frequency cautery power supply 2B, thus constructed, feed power to the return electrode 32 and the coagulating electrode 33 during the coagulation operation as shown in FIG. 10A. The switch 36 is turned to the coagulation operation side. The high-frequency cautery power supply 2B performs the coagulation operation in accordance with the power control of the high-frequency power already discussed in connection with the first and second embodiments.

Subsequent to the coagulation process, the high-frequency power is fed to the incising electrode 34 and the return electrode 32 as illustrated in FIG. 10B. The switch 36 is turned to the incision operation side. While the incising electrode 34 and the return electrode 32 are powered, the incising electrode 34 is projected out of the coagulating electrode 33 to incise the body tissue.

Since the conduction pathway is switched within the electrosurgical device to change between the coagulation process and the incision process, the ease of use is improved eliminating the need for interchanging the coagulating electrode 33 or the incising electrode 34.

In combination with the power control of the high-frequency power discussed in connection with the first and second embodiments, the incising electrode 34 is automatically selected subsequent to the coagulation operation. In such a case, the control circuit 28 discussed in connection with the first embodiment may control the switch 36 of the high-frequency cautery power supply 2B and the projecting mechanism of the incising electrode 34 of the coagulating and incising electrodes 30. This arrangement further improves the ease of use.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electrosurgical device for treating a body tissue with a high-frequency power, comprising:

an electrode for outputting a high-frequency power to the body tissue for treatment; and a high-frequency cautery power supply having a control circuit for controlling a high-frequency power generator that outputs the high-frequency power to the electrode, wherein the control circuit of the high-frequency cautery power supply comprises:

a time measurement unit for measuring output time of the high-frequency power when a first high-frequency power is applied to the body tissue, from said high-frequency cautery power supply, the time measurement unit being able to set the output time to a desired output time;

an impedance detector for detecting an impedance of the body tissue in the coagulated state thereof when the body tissue is treated using the high-frequency power applied from the electrode, an impedance comparator for: a) determining whether a change with the passage of time of the impedance which is detected by said impedance detector meets a predetermined condition within the output time set by the time measurement unit; and b) for comparing the impedance of the coagulated tissue detected by the impedance detector with an impedance predetermined for the purpose of the treatment of a region to be treated; and a high-frequency power switch for switching the applied first high-frequency power output of the high-frequency power generator to a second high-frequency power level when the output time set in the time measurement unit has elapsed, or, for switching the applied first high-frequency power to a third high-frequency power level when a change with the passage of time of the impedance detected by the impedance detector meets a predetermined condition within the output time as set by the time measurement unit, wherein said high-frequency power switch further switches the second or third high-frequency power level to a fourth high-frequency power level if the impedance becomes higher than the predetermined impedance after the first high-frequency power level has been switched to the second or third high-frequency power level, and wherein a volume of the body tissue subject to said high-frequency power control is determined in accordance with the output time measured and the change with the passage of time of the impedance.

2. An electrosurgical device according to claim 1, wherein the control circuit performs constant power control of the high-frequency power generator based on a value predetermined in accordance with the result of comparison provided by the impedance comparator.

3. An eleotrosurgical device according to claim 2, wherein said time measurement unit includes means for determining when said high-frequency power output time exceeds said set output time, the control circuit controls the high-frequency power generator to increase application of high-frequency power during said treatment by a predetermined value to said second high-frequency output power level when the set output time is exceeded.

4. An electrosurgical device according to claim 3, wherein said impedance comparator includes means for determining when a tissue impedance successively obtained exceeds one or more predetermined values, the control circuit controls the high-frequency power generator to output a high-frequency power to said third high-frequency power level that is lower in level than the initial high-frequency power by a predetermined value when said tissue impedance successively obtained exceeds said predetermined value of the tissue impedance and ten controls the high-frequency power generator to stop outputting the high-frequency power when the tissue impedance increases above another predetermined value.

5. An electrosurgical device according to claim 2, wherein the control circuit further comprises voltage sensor means for sensing an output voltage level, and comparing said sensed level against a predetermined voltage, said control circuit controlling the high-frequency power generator to stop outputting the high-frequency power when the output voltage of the high-frequency power drops below said predetermined voltage.

6. An electrosurgical device according to claim 2, wherein the control circuit further comprises voltage sensor means for sensing an output voltage level, and comparing said sensed level against a predetermined voltage, said control circuit controlling the high-frequency power generator to output a high-frequency power to a level lower than an initial high-frequency power level by a predetermined value when the output voltage of the high-frequency power is above said predetermined voltage.

7. An electrosurgical device according to claim 1, wherein said time measurement unit includes means for determining that said high-frequency power output time is within said set output time, the control circuit controls the high-frequency power generator to output a corresponding high-frequency power, from among the plurality of constant-power, high-frequency powers, in accordance with the comparison result of the impedance comparator when the output time measured of the high-frequency power is within said set output.

8. An electrosurgical device according to claim 7, wherein said impedance comparator includes means for determining when a tissue impedance successively obtained exceeds a minimum value of the tissue impedance, the control circuit controls the high-frequency power generator to output a high-frequency power to said third high-frequency power level that is lower in level than an initial high-frequency power by a predetermined value when a tissue impedance successively obtained exceeds said minimum value of the tissue impedance.

9. An electrosurgical device according to claim 1, wherein said impedance comparator includes means for determining when a tissue impedance successively obtained exceeds one or more predetermined values, the control circuit controls the high-frequency power generator to successively reduce high-frequency power output from initial said third high-frequency power in level by a predetermined value to said fourth high-frequency power level when a tissue impedance successively detected exceeds a first predetermined value of the tissue impedance and then controls the high-frequency power generator to stop outputting the high-frequency power when the tissue impedance becomes above a second predetermined value.

10. An electrosurgical device according to claim 1, wherein the control circuit determines a volume or the coagulated state of the body tissue held by the electrode based on an initial voltage just after the high-frequency power is started to be outputted.

11. An electrosurgical device for treating a body tissue with a high-frequency power, comprising:

an electrode for outputting a high-frequency power to the body tissue for treatment; and a high-frequency cautery power supply having a control circuit for controlling a high-frequency power generator that outputs the high-frequency power to the electrode, wherein the control circuit of the high-frequency cautery power supply comprises;

a time measurement unit for measuring suspension time of the high-frequency power applied to the body tissue, and a counter unit for counting a number of discrete applications of high-frequency power, a count of said number of discrete applications being initialized prior to high-frequency power output;

an impedance detector for detecting an impedance of the body tissue in the coagulated state thereof when the body tissue is treated using the high-frequency power applied from the electrode, said impedance detector detecting impedance based on body information such as the temperature of the body tissue;

an impedance comparator for comparing the impedance of the coagulated tissue detected by the impedance detector with an impedance predetermined for the purpose of the treatment of a region to be treated;

a high-frequency power switch for switching the output of the high-frequency power generator based on the result of comparison provided by the impedance comparator, said switch temporarily suspending application of said high-frequency power for a predetermined time based on the impedance monitored; and, means for comparing said count against a predetermined count;

said control circuit enabling a further discrete application of a high-frequency power from an electrode to the body tissue for treatment at a reduced power level if said compared count is less than said predetermined count, said count of said discrete application of high-frequency power being incremented when said high-frequency power application is applied at said reduced power level, wherein said control circuit controls repeated application of said high-frequency power at successively reduced levels while said count is less than said predetermined count.

12. An electrosurgical device according to claim 11, wherein a coagulated state value is predetermined by an operator.

13. An electrosurgical device according to claim 11, wherein the control circuit further comprises means for changing a control mode from constant power control to constant-voltage control when the initial output voltage of the high-frequency power exceeds a predetermined voltage.

14. An electrosurgical device according to claim 11, wherein the control circuit controls the high-frequency power generator to temporarily suspend the outputting of the high-frequency power for a predetermined duration of time and then to output a high-frequency power lower in level than an initial high-frequency power by a predetermined value when the initial output voltage of the high-frequency power output is below a predetermined voltage and when a tissue impedance is larger than the minimum value of the tissue impedance, is larger than the double of the minimum value of the tissue impedance, and is smaller than a predetermined value.

15. A method of controlling an electrosurgical device for treating a body tissue with a high-frequency power, comprising the steps of:

outputting a high-frequency power from an electrode to the body tissue for treatment;

monitoring an impedance of the body tissue in the coagulated state thereof when the body tissue is treated using the high-frequency power applied from the electrode;

measuring output time of the high-frequency power;

increasing the high-frequency output if the output time measured reaches a predetermined time before the impedance monitored exceeds a predetermined value; and decreasing the high-frequency output if the impedance monitored exceeds a predetermined value before the output time measured reaches a predetermined time.

16. A method of controlling an electrosurgical device for treating a body tissue with a high-frequency power, comprising the steps of:

initializing a count of a discrete application of high-frequency power;

outputting said high-frequency power from an electrode to the body tissue for treatment;

monitoring an impedance of the body tissue in the coagulated state thereof when the body tissue is treated using the high-frequency power applied from the electrode;

temporarily stopping outputting the high-frequency power for a predetermined time based on the impedance monitored;

incrementing said discrete application count of high-frequency power and comparing said count against a predetermined count:

outputting a high-frequency power from an electrode to the body tissue for treatment at a reduced power level if said count is less than said predetermined count; and repeating said monitoring, temporarily stopping, incrementing and outputting steps while said count is less than said predetermined count.

* * * * *